United States Patent [19]

Durack

[11] Patent Number: 4,492,761

[45] Date of Patent: Jan. 8, 1985

[54] COMPLEMENT ASSAY METHOD

[75] Inventor: David T. Durack, Durham, N.C.

[73] Assignee: Duke University, Durham, N.C.

[21] Appl. No.: 365,334

[22] Filed: Apr. 5, 1982

[51] Int. Cl.$^3$ .......................... C12Q 1/18; C12Q 1/34; C12N 1/06; C12N 1/20

[52] U.S. Cl. ..................................... 436/519; 436/63; 436/821; 435/4; 435/7; 435/18; 435/29; 435/32; 435/253; 435/259; 435/810; 435/849

[58] Field of Search .................... 435/4, 18, 32, 29, 34, 435/38, 253, 259, 810, 849; 436/63, 821, 519, 507; 424/93

[56] References Cited

U.S. PATENT DOCUMENTS

| | | | |
|---|---|---|---|
| 3,834,991 | 9/1974 | Megraw et al. | 435/18 |
| 3,870,601 | 3/1975 | Warren et al. | 435/253 |
| 3,880,715 | 4/1975 | Schneider | 435/29 |
| 3,910,824 | 10/1975 | Cartwright et al. | 435/4 |
| 4,065,354 | 12/1977 | Ullman et al. | 435/7 |
| 4,104,126 | 8/1978 | Young | 435/4 |
| 4,130,634 | 12/1978 | Molinaro et al. | 436/828 |
| 4,239,746 | 12/1980 | Bartos et al. | 436/808 |
| 4,242,447 | 12/1980 | Findl et al. | 435/18 |
| 4,255,517 | 3/1981 | Ford | 435/4 |
| 4,288,539 | 9/1981 | McAleer et al. | 435/34 |
| 4,303,752 | 12/1981 | Kolehmainen et al. | 435/18 |

FOREIGN PATENT DOCUMENTS

| | | | |
|---|---|---|---|
| 25351 | 3/1981 | European Pat. Off. | 435/34 |
| 2423541 | 12/1979 | France | 435/35 |

OTHER PUBLICATIONS

Fundenberg et al., "Basic and Clinical Immunology" 2nd edition, Lange Medical Publishers (1978), pp. 370-373, 220, and 600.

Yasuda et al., "A Simple Method to Measure Anti-Glycolipid Antibody by Using Complement-Mediated Immune Lysis of Fluorescent . . ." Journal of Immunological Methods 44 (9-1981), pp. 153-158.

D'Orazino et al., "Potentiometric Electrode Measurement of Serum Antibodies Based on the Complement Fixation Test" Analytica Chemica Acta 109 (1979), pp. 25-31.

Snyderman et al., "Deficiency of the Fifth Component of Complement in Human Subjects" American Journal of Medicine 67 (10-1979), pp. 638-645.

Pelczar et al., "Manual of Microbiological Methods" McGraw Hill Inc. NY, (1957), pp. 215-223.

*Primary Examiner*—Lionel M. Shapiro
*Assistant Examiner*—John E. Tarcza
*Attorney, Agent, or Firm*—Oblon, Fischer, Spivak, McClelland & Maier

[57] ABSTRACT

A method of determining (1) the activity of complement, (2) the bacteriolytic activity of serum, or (3) the titer of antibody in a sample which comprises: (a) incubating complement-sensitive microorganisms containing an assayable intracellular component with the sample, and (b) detecting the assayable component released into the sample by lysis of the microorganisms.

16 Claims, 1 Drawing Figure

COMPLEMENT ASSAY METHOD

BACKGROUND OF THE INVENTION

1. Field of the Invention

The present invention relates to a complement dependent bactericidal assay useful for the measurement of complement, bactericidal properties of serum, and immune components of serum.

2. Brief Description of the Prior Art

A complex of proteins, which is known as complement and is abbreviated as C', is present in the fresh serum of vertebrates, is bound by antigen/antibody aggregates, and plays an important auxiliary role in antigen/antibody interactions and in host defense. Complement consists of nine major components and nine or more other components that react in a known sequence when antigen/antibody combine. C' reacts at the sites of antigen/antibody combination on cell membranes to cause lysis. In the case of erythrocytes this causes the release of hemoglobin into solution, an effect which is called hemolysis.

Certain gram-negative bacteria coated with specific antibody can be lysed by C' acting through the same reaction sequence as in red cell lysis. Gram-positive bacteria and mycobacteria, however, do not appear to be susceptible to the lytic reaction of complement, although their resistance is not well understood. The lysis of gram-negative bacteria by C' is known as the bactericidal effect of complement. (See, for example, Eisen, "Immunology. An Introduction to Molecular and Cellular Principles of the Immune Responses," 2nd edition, Harper & Rowe Publishers, Inc., 1974, pp. 513–523; and Kabat, "Structural Concepts in Immunology and Immunochemistry," Holt, Reinhardt & Winston, Inc., 1968, pp. 46–48).

The hemolytic properties of complement have been used in the complement fixation assay, an important laboratory procedure for detecting and measuring many different kinds of antigens and antibodies. Thus, if sheep erthyrocytes are optimally coated with non-agglutinating amounts of antibodies to the cells, the addition of C' and the presence of adequate concentration of Mg++ and Ca++ ions promptly causes the cells to lyse. The extent of lysis is evaluated qualitatively by inspection, or quantitatively by determining the concentration of supernatant hemoglobin after sedimentation of intact cells and stroma. These methods have been utilized to measure immune components of serum, for example by Molinaro et al, U.S. Pat. No. 4,130,634 and Bartos et al, U.S. Pat. No. 4,239,746, which are herein incorporated by reference.

A general test for the assay of antibodies and antigens, albeit without using complement, has been described by Young, U.S. Pat. No. 4,104,126, wherein an antigen is conjugated with a bacteriophage, and the conjugate allowed to compete with the antigen in the specimen under assay for a number of binding sites on antibody. The phage conjugates surviving antibody inactivation are quantified by determining intracellular constituents of host bacteria subsequently infected by the bacteriophage remaining viable, and which can be related to the levels of antigen originally present in the specimen. For example, a colorimetric assay for β-galactosidase freed by phage lysis of *E. coli* is described in Young (column 5), and the possibility is mentioned of increasing the released enzyme by induction.

The complement hemolytic assay is somewhat limited in its approach in that it always requires sheep red blood cells and it does not measure bacteriolysis, thereby being meaningless in assessing the patient's natural defenses against infection. A bacteriolytic assay such as that of Young, also fails to determine the total bacteriolytic properties of the serum itself, since bacteriolysis is carried out with an externally added conjugate containing phage.

Therefore a need continues to exist for an efficient, safe and sensitive assay for the detection of the bacteriolytic properties of a sample and measurement of other immune components.

SUMMARY OF THE INVENTION

It is therefore an object of the invention to provide a method for the determination of complement activity in a sample.

It is another object of the invention to provide a method for the determination of the total bacteriolytic properties of a sample.

It is another object of the invention to provide a method for the determination of immune components, such as antibodies or antigens in a sample.

These and other objects of the invention as will hereinafter become more readily apparent have been attained by providing a method of determining complement activity in a sample comprising:

incubating complement-sensitive microorganisms containing an assayable intracellular component with said sample and detecting said assayable component released into solution from lysed microorganisms.

Another object of the invention has been attained by providing a method for determining the bacteriolytic properties of a sample which comprises:

incubating said sample with microorganisms containing an assayable intracellular component, and detecting said assayable component released into solution from lysed microorganisms.

DESCRIPTION OF THE PREFERRED EMBODIMENTS

Figure 1:
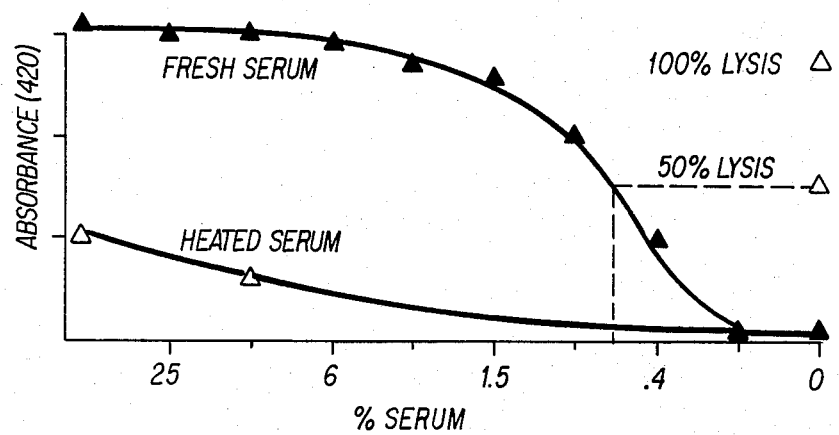
FIG. 1 shows the variation of absorbance at 420 nm (O-nitrophenol) caused by the hydrolysis of ONPG by β-galactosidase released from *E. coli* upon lysis with complement containing fresh (—▲—) and heated (—△—) serum. CB50 for normal human serum (NHS) using *E. coli* ATCC 39056 is 116.2±13.6 (mean±S.D.) and using *E. coli* ATCC 15224 is 17.3±2 (mean±S.D.).

The present invention represents an alternative to the standard hemolytic assay for the detection of complement activity in samples, i.e., the assay using red blood cells (RBC's). In the present invention, instead of RBC's, the assay utilizes complement-sensitive microorganisms, especially complement-sensitive bacteria. Instead of measuring the appearance of red color due to the release of hemoglobin from erythrocytes, the present method utilizes the release of an assayable intracellular component due to the lysis of the microorganisms. As will become more readily apparent below, in the preferred embodiment, the assayable component is one whose intracellular level can be greatly increased due to pre-assay manipulation of the microorganism such as, for example, by induction.

The term "microorganisms" as used in the present invention is meant to include any microorganism which is sensitive to lysis by complement. Most commonly, such microorganisms are gram-negative bacteria. Some gram-negative bacteria coated with antibody are known to be lysed by complement via a similar reaction sequence to RBC lysis. Most gram-positive bacteria and mycobacteria, however, are not susceptible to the lytic action of C'. Their resistance is probably due to peculiarities of their cell wall, because protoplasts of gram-positive bacteria are readily lysed by C'. Thus, such protoplasts are also included in the present invention under the term "microorganisms".

Among the gram-negative bacteria which may be used in the present invention are those of the following genera: Neisseria, Veillonella, Brucella, Bordetella, Pasteurella, Haemophilous, Escherichia, Erwinia, Shigella, Salmonella, Proteus, Yersinia, Enterobacter, Serratia, Azotobacter, Rhizobium, Nitrosomona, Nitrobacter, Thiobacillus, Pseudomonas, Acetobacter, Photobacterium, Zymomonas, Aeromonas, Vibrio and Desulfovibrio. Among the most preferred, because of free availability and thorough knowledge thereof are those of the genus Escherichia, most particularly *Escherichia coli*.

The microorganisms used in the present invention have to be "complement-sensitive", meaning that they should be lysable by complement present in normal human or animal serum. It is known in the art that, for example, not every strain of a gram-negative bacterium will be serum sensitive. Thus, it is known that about $\frac{2}{3}$ of all *E. coli* strains are complement-sensitive. However, the determination of the complement sensitivity of any given microorganism can be routinely carried out by those of skill in the art by a simple test. Thus, any strain of the microorganism can be incubated under standard conditions with serum containing known active complement, and antibody, and after a predetermined time, tested for viability. For some strains lysis by complement may be carried out in the absence of antibody. For these strains, antibody is important but is not believed to be essential. Natural antibody for *E. coli* is found in the serum of nearly all normal humans. Specific antibody can be added to the test if desired.

The present invention detects activity of complement in a sample by its effects on the lysis of microorganisms. C'-mediated lysis of microorganisms is detected by assaying for any intracellular assayable component. Such assayable components may include, for example, intracellular enzymes, coenzymes such as NAD, NADH, TPP or FAD, nucleic acids, such as DNA or RNA, and other substances such as ATP. As is disclosed in Young, U.S. Pat. No. 4,140,126, herein incorporated by reference, all such materials admit of spectrophotometric determination of one sort or another, and indeed, various of them can be measured either by absorption or by emission spectrometry. For example, ATP can be fluorometrically determined by its mediation of a luciferin-firefly luciferase reaction whose product luciferyl adenylate fluoresces on oxidation. Intracellular DNA can be monitored by ultra-violet spectroscopy. For a number of reasons, the use of colorimetric techniques to monitor intracellular constituents exposed to cell lysis is preferred. In the most preferred embodiment of this invention, this spectrophotometric determination is carried out by assaying the activity of an intracellular enzyme. In this mode, an excess of the enzyme substrate is added to the sample under test and rapid turnover yields quick quantifiable results. A substrate, which upon enzyme action releases a product which has optical density at a different wavelength or of a different magnitude than the substrate itself, is normally utilized. Thus, for example, one may assay for the enzyme $\beta$-galactosidase by adding ortho-nitrophenyl $\beta$-galactoside (ONPG) which yields orthonitrophenol. Other possible enzymes and substrate-product pairs are: alkaline phosphatase, assayed with p-nitrophenyl phosphate releasing paranitrophenol; asparaginase acting on L-asparagine and determinable by the biuret method; glutaminase acting on glutamine producing ammonia determinable by the biuret method, and others such as cytochrome C, peroxidase, catalase, $\beta$-glucuronidase, $\beta$-glucosidase, glucose oxidase, galactose-oxidase and the like. In general, many of the myriad of enzymes derived from microorganisms which are used in enzyme immunoassay tests, and known to those skilled in the art, could be utilized.

The component to be assayed should be intracellular, i.e., should be released from the microorganism only upon complement-mediated lysis. Preferably, the component should be truly cytoplasmic, although periplasmic components can be used, provided any possible background leakage thereof into the surrounding medium can be readily accounted for.

In the preferred embodiment of the present invention, the intracellular assay component is one whose concentration level in the intracellular medium can be increased greatly above normal (wild type) levels by preassay manipulations of the microorganism. For example, it is well-known that the levels of alkaline phosphatase can be greatly increased in *E. coli* by growing the bacterium in phosphate limiting growth medium. Under these conditions, up to about 6% of the cell protein is alkaline phosphatase. Another common procedure for increasing the level or activity of an intracellular component is by induction. In the case of an enzyme, it is possible to induce in any given microorganism levels of said enzyme in excess of that ordinarily present, as by culturing the bacteria in the presence of an excess of natural or synthetic substrate for the enzyme. For example, the $\beta$-galactosidase content of *E. coli* can be increased 10,000-fold by culturing the bacteria with lactose as the only carbon source. Many strains of bacteria contain induceable enzymes. Moreover, there exist bacterial strains which are "constitutive" for given enzymes. These are mutant strains which would contain thousands of times the enzyme present in the corresponding wild type organism. Production of these mutant strains is especially convenient where it is desired that the mutant be constitutive for a colorimetrically determinable enzyme.

Virtually any microorganism which can be made to induce the synthesis of an enzyme could be used. It is readily ascertainable to those of skill in the art whether a given strain of a microorganism can be made to induce a given enzyme. The organism is grown in the presence of an inducer for a predetermined period of time, the inducer is then removed, the organism is lysed, a substrate for the induced enzyme is added, and the levels of the enzyme are measured. A number of $\beta$-galatosidase constituitive *E. coli* strains are known, for example, ATCC 15224. Another strain useful in the present invention is ATCC 39056, deposited on March 1, 1982.

The word "detecting", as used in the present invention and claims, implies that the intracellular component is measured by any standard measurement technique, most preferably, when it is an enzyme, by an enzyme assay technique. As mentioned previously, however, other colorimetric techniques or even radiometric techniques might be utilized.

The complement mediated lysis procedure of the present invention can be utilized, for example, for determining the bacteriolytic properties of any given sample, especially the bacteriolytic properties of animal serum, most preferably human serum.

Another use of the technique of the invention is in a complement fixation test, wherein the titers of antibody in a sample are detected in analogy to the red blood cell complement fixation tests of the prior art, but utilizing microorganisms instead.

The antibody assay of this invention is normally performed in two stages. In stage one, antiserum and antigen are mixed in the presence of a carefully measured amount of complement and incubated, usually overnight at about 4° C. If the appropriate antibody/antigen complexes are formed, then complement is inactivated or "fixed". In stage two, a suspension of microorganisms is added to determine whether active complement has survived. Microorganism lysis and release of the intracellular component followed by assay, indicates that the complement persists and, therefore, that an effective antibody/antigen reaction has not occurred in stage one. Conversely, absence of intracellular component release indicates that complement has been fixed, and therefore, that an antibody/antigen reaction has occurred in stage one.

With a known antigen, an assay can be used to detect and measure antibodies in unknown samples; and with a standard antiserum to a known antigen it can be used to detect antigen in complex biological materials. (See Eisen, "Immunology", pp. 512–515, supra.)

In a standard complement activity or bacteriolytic assay, the conditions of incubation, such as times, concentrations, temperatures, addition of antibodies (e.g., IgM) and the like, can be readily ascertained by those of skill in the art without undue experimentation. Incubation occurs for a time effective to produce a detectable amount of lysis in the microorganisms, and is normally in the range of about 5 minutes to 2 hours. Temperature conditions range from about 4° C. to temperatures below that at which complement would be inactivated, namely about 50° C.–56° C.; 35° C.–37° C. is preferred. The number of microorganisms to be added will depend on the volume of sample to be tested, but ranges from $10^5$ to $10^9$, most preferably $10^6$–$10^7$ cells/ml. When the intracellular component released is an enzyme, which is to be assayed by use of a chromogenic substrate, the substrate can either be present in the original sample, or be added at the end of the lysisproducing incubation. In either event, it is useful when quantitative analyses of complement, antibody or antigen is desired, to carry out a series of trials with varying concentrations of the reagents to ascertain the optimum level of chromogenic substrate to be added. The techniques then follow those well-known techniques useful in general in immunoassay methodology.

The complement activity or bacteriolytic effect of any sample can be tested. Preferably, a sample is liquid or semi-solid such as urine, saliva, serum, tissue samples, feces and the like. Solid samples can be dispersed or dissolved in appropriate solutions for assay. Preferably, the samples are serum samples, most preferably human serum samples.

The materials for use in the assay of the invention are ideally suited for the preparation of a kit. Such a kit may comprise a carrier means being compartmentalized to receive in close confinement one or more container means such as vials, test tubes, and the like, each of said container means comprising one of the separate elements to be used in the method. For example, one of said container means may comprise microorganisms, either in suspension or, most preferably, freeze-dried, and may also include a predetermined amount of chromogenic substrate when and if the intracellular assayable component is an enzyme. Alternatively, the substrate may be present in a second container means and a compartmentalized carrier, either in an appropriate physiologically acceptable solution or in lyophilized form. The carrier can also contain, in addition, a third container means comprising antibody useful to initiate the complement lysis reaction, as well as another container means comprising the agents necessary to carry out standard controls for the complement fixation such as, for example, to ascertain that the antigen or antiserum to be tested are not anticomplementary, i.e., that each does not inactivate complement without the other. The carrier may also contain a plurality of container means, each of which comprises different levels of complement, the combination being useful to prepare a standardized curve.

If the first container means comprises both the microorganisms and a chromogenic substrate, all the user has to do is add a premeasured amount of sample containing the measurable amount of complement in a buffer to the first container means, or the whole into a separate container means. Incubation is then allowed to proceed as previously and thereafter, lysis is detected by measuring the amount of colored product.

A different kit can be prepared for complement fixation determinations, for bacteriolytic serum efficiency or for the detection of antigens or antibodies.

Among the many clinical applications to which the present methodology can be applied are the routine measurement of human complement activity, especially in infectious diseases, routine testing of total human serum, bacteriolytic capacity in neonates and/or immunocompromised patients; complement fixation assays; identification of functional antibody deficiencies; assay of anticomplementary factors in serum, especially immunocomplexes, and the like. Among the many advantages of the present methodology over hemolytic assays based on sheep red blood cells are the rapidity, since the test takes less than 2 hours versus 3–4 hours for the SRBC complement assay; potential for automation, since the present test should be easily automated, reducing the time required even further to about one hour or less; micromethodology, since the test can be run in microtiter plates versus test tubes for the SRBC assay; and the possibility of using freeze-dried microorganisms which can be stored indefinitely. These are easier to maintain than sheep red blood cells, or even a live source of such cells.

Having now generally described this invention, the same will be better understood by reference to certain specific examples, which are included herein for purposes of illustration only and are not intended to be limiting unless otherwise specified.

EXAMPLE 1

C'-sensitive *E. coli* (ATCC 39056 or ATCC 15224) was grown on an agar containing isopropyl- $\beta$-D-thiogalactopyranoside (IPTG) to induce β-galactosidase. *E. coli* ATCC 39056 is a highly serum sensitive smooth strain of *E. coli* that was originally isolated from human urine. *E. coli* ATCC 15224 is a well known experimental strain that is constitutive for β-galactosidase. Both strains have been in use for years and are maintained by bi-weekly subculture on nutrient agar with IPTG. The organisms are stored at −70° C. in a medium containing 80% trypticase soy broth and 20% glycerol. Lyophilyzed reserves of these *E. coli* strains are kept in case the agar plate becomes contaminated. 16 to 24 hours before the assay *E. coli* is streaked on a nutrient plate containing 0.1 mg/ml of IPTG.

Reagents (a) Buffer: phosphate buffered saline (PBS) pH 7.4 was filtered and stored at 4° C.;
(b) Substrate: ortho-nitro-phenyl- β-galactoside (ONPG) in sodium phosphate buffer, pH 7.0 (2 mg/ml) was filtered and stored at 4° C.;
(c) Sodium carbonate (1.0 M) was filtered and stored at 4° C.;
(d) Normal human serum and test human serum
   (1) Not heat inactivated: stored at −70° C.;
   (2) Heat inactivated for 30 minutes at 56° C.: stored at −20° C., or −70° C.

PROCEDURE (a) Preparation of *E. coli* suspension:
   (1) The growth of *E. coli* was removed with a sterile swab from the surface of a nutrient agar plate containing IPTG, and the swab was swirled in a 15 ml tube containing 6-8 mls of PBS;
   (2) The suspension of *E. coli* was centrifuged at 4700 rpm for 7 minutes at room temperature, the supernatant was decanted, and *E. coli* was resuspended in 6-8 mls PBS;
   (3) *E. coli* was washed twice in PBS;
   (4) *E. coli* was resuspended in PBS until absorbance had reached 0.5±0.01 at 540 nm using a spectrophotometer;
   (5) *E. coli* was kept on ice until used in the assay.
(b) Preparation of Human Sera
   (1) Normal serum was used for control, to provide 100% lysis of *E. coli* and a standard lysis curve if desired.
     (a) Blood was collected in vacutainers and allowed to clot for 30 minutes at room temperature;
     (b) Clotted blood was centrifuged at 4,500 rpm for 10 minutes.
     (c) Serum was decanted and stored in 0.40 ml and 1.0 ml aliquots at −70° C.;
     (d) Just before the assay the sera was thawed in a 37° C. water bath and placed on ice until use in the assay.
     (e) Two 50 μl aliquots were heat-inactivated at 56° C. for 30 minutes.
   (2) Test serum
     (a) Steps (a) through (e) above were followed.
(c) Assay: 4 serum samples/microtiter plate (See Table 1 below; directions are for 1 sample)
   (1) PBS was added to wells;
   (2) Serum (heated or unheated) was added to appropriate wells in duplicate;
   (3) *E. coli* was added to wells;
   (4) Plate was shaken on a jogger at appropriate speed for 1 minute between each step;
   (5) A mylar cover sheet was placed on the plate and the same was incubated in a 37° C. water bath for 30 minutes;
   (6) The plate was removed from the water bath, the cover was removed from the plate and 25 microliters of ONPG (2 mg/ml) was added to all wells;
   (7) The plate was shaken on a jogger at appropriate speed for 1 minute;
   (8) Cover sheet was placed on the plate, and the plate was incubated in a 28° C. water bath for 15 minutes;
   (9) The plate was removed from the water bath, the cover was removed from the plate and 125 microliters of 1.0 M sodium carbonate was added;
   (10) The plate was shaken on a jogger at an appropriate speed for about 1 minute;
   (11) The plate was read with a "Multiskan" (TM; Flow Labs) using a 420 mm filter.

TABLE 1

| Layout of wells in Microtiter plate, for standard test | | | |
|---|---|---|---|
| Well | Final % Serum | *E. Coli* ul/well | Final vol ul/well* |
| 1 | 50 | 10 | 100 |
| 2 | 25 | 10 | 100 |
| 3 | 12.5 | 10 | 100 |
| 4 | 6.25 | 10 | 100 |
| 5 | 3.125 | 10 | 100 |
| 6 | 1.56 | 10 | 100 |
| 7 | .78 | 10 | 100 |
| 8 | .39 | 10 | 100 |
| 9 | .2 | 10 | 100 |
| 10 | 0 | 10 | 100 |
| 11 | 50 | 10 | 100 |
| 12 | 6.8 | 10 | 100 |

*made up with PBS

β-galactosidase released by lysis was assayed by addition of the substrate o-nitrophenyl galactopyranoside. The resulting yellow color was measured at 420 nm. A standard serum giving 100% lysis, and a background curve using heated serum is shown in FIG. 1. The 50% point on the S shaped lytic curve provides a numerical assay for the serum bacteriolytic activity ($CB_{50}$). Lysis is complete by 20 minutes; optimum pH range is 7.0–7.4; added lysozyme raises the bacteriolytic effect slightly; aggregated immunoglobulin and addition of 2-mercaptoethanol inhibits the bacteriolytic activity in this system.

EXAMPLE 2

Estimation of Various Factors on the Bacteriolytic Assay

100% Lysis of *E. coli*. Concentrations of normal human serum ("NHS") ranging from 0.2% to 50% were incubated with *E. coli* for 30 minutes before addition of ONPG. Complete lysis of *E. coli* occurred with 6% NHS.

Kinetics. To determine minimal time for 100% lysis of *E. coli* by NHS and subsequent release of β-galactosidase, *E. coli* was incubated with 12% non-heated serum for 0, 3, 5, 7.5, 15, 22.5, 30, 45, 60, 75 and 90 minutes before the addition of 100 micrograms of ONPG. By 22.5 minutes of incubation, 100% of *E. coli* was lysed by 12% NHS. To discern the effect of incubation length upon the $CB_{50}$ (50% lysis of *E. coli*), *E. coli* was incubated with 1.5%, 0.8% and 0.4% NHS for various time periods. Due to the limited lysis of *E. coli* by these sera concentrations and subsequent proliferation of *E. coli*, increasing the time of incubation also raised the $CB_{50}$. To allow sufficient time for 100% lysis without excessive multiplication of *E. coli* within the $CB_{50}$ range, a standard incubation time of 30 minutes can be chosen.

ONPG and *E. coli* Titration. In the $CB_{50}$ assay, complete lysis of *E. coli* by 12% NHS must occur with the substrate, ONPG, in excess to obtain a 100% lysis reading. Therefore, both *E. coli* and ONPG were titrated in checkerboard fashion with 12% NHS. Briefly, *E. coli* was resuspended in PBS until an absorbance of 0.500 was reached. 20 microliters, and 20 microliters of undiluted plus 10 microliters of a 1:2 and a 1:4 diluted suspension of *E. coli*, were incubated with 12% NHS for 30 minutes followed by addition of 400 micrograms, 200 micrograms, 100 micrograms, 50 micrograms or 25 micrograms of ONPG. 50 micrograms of ONPG were found to be in excess when incubated with 10 microliters of undiluted *E. coli*. With excess ONPG (100 micrograms), complete but optimal lysis of *E. coli*, as detected by an absorbance of less than 2,000 occurred with 10 microliters of undiluted *E. coli*. To determine the effect of *E. coli* and ONPG concentration upon the $CB_{50}$, all doses of *E. coli* and ONPG mentioned above were assayed with 1.5%, 0.8% and 0.4% non-heated serum. Using excess ONPG with the standard concentration of *E. coli* (10 microliters at 0.5 nm) resulted in $CB_{50}$ values from 139 to 75, all within the normal range. Higher $CB_{50}$ values were obtained with lower concentration of *E. coli* because less serum was needed to lyse 50% *E. coli*.

Ionic Strength. To study the effect of ionic strength upon lysis of *E. coli* by non-heated serum, the serum concentration must be limited so that 100% lysis of *E. coli* does not occur at the physiological ionic strength of 0.16. Briefly, *E. coli* was incubated for 30 minutes with 0.8% and 0.4% NHS in PBS having the ionic strengths: 0.027, 0.06, 0.09, 0.12, 0.16, 0.20 and 0.24. Optimal lysis of *E. coli* by NHS occurred with 0.06, 0.09 and 0.12 ionic strength buffers. Likewise the lysis of *E. coli* without serum was more pronounced with these same buffers in addition to 0.027 ionic strength buffers. In contrast, 0.027, 0.20 and 0.24 ionic strength buffers partially inhibited lysis of *E. coli* by NHS when compared to PBS at physiological ionic strength.

pH and Molarity. To determine the effect of pH and molarity upon lysis of *E. coli* by NHS as reflected in the $CB_{50}$, 10 microliters of *E. coli* (absorbance 1.0) was incubated for 30 minutes with 12%, 6%, 3%, 1.5%, 0.8%, 0.4% and 0.2% NHS in both 0.01 M and 0.04 M PBS, ionic strength 0.16 at pH 6.0, 6.5, 7.0, 7.4 and 7.9. Independent of molarity, the $CB_{50}$ peaked with pH 7.0 and pH 7.4 buffers, dropped sharply with the acidic buffers, and declined slightly with the alkaline buffer. Background lysis of *E. coli* was not affected by changes in either pH or molarity.

Effect of Lysozyme upon Lysis of *E. coli* by NHS. The bacterial cell envelope of *E. coli* consists of an innermost cellular membrane, surrounded by a layer of peptidoglycan, which is covered by a layer of lipopolysaccharide and lipoprotein, and an outermost polysaccharide capsule. In addition to lysis of *E. coli* by antibody and complement, lysozyme, which is present in low concentrations in NHS but concentrations 10-fold higher in some leukemic sera, may play an important role in lysis of *E. coli* due to its ability to degrade peptidoglycan. To test the effect of additional lysozyme upon lysis of *E. coli* by NHS as reflected in the $CB_{50}$, concentrations of lysozyme between 0.1 micrograms and 30.0 micrograms were mixed with NHS before the addition of 10 microliters of *E. coli* (absorbance 1.000). All concentrations of lysozyme tested enhanced the $CB_{50}$ with greater enhancement occurring with larger doses of lysozyme. Titrating concentrations of lysozyme found in leukemic sera with NHS in the $CB_{50}$ assay showed a 13% to 20% increase in the $CB_{50}$. (Conditions of assay at this time gave a normal $CB_{50}$ around 100).

Having now fully described this invention, it will be apparent to one of skill in the art that the same can be performed within a wide and equivalent range of conditions, parameters, concentrations, temperatures, microorganism cells, samples, and the like, without affecting the spirit or scope of the invention, or of any embodiments thereof.

What is claimed as new and intended to be covered by letters patent of the United States is:

1. A method of determining the bacteriolytic capacity of a sample, which comprises:
    (a) incubating a mixture comprising (1) an aqueous suspension of *E. coli* ATCC 39056 bacteria at a concentration of from $10^5$ to $10^9$ cells/ml, said cells containing an assayable intracellular component, and (2) a biological sample in the presence of complement, wherein said mixture contains from 0.2 to 50% by volume of said sample and said incubating is conducted at a temperature of at least 4° C. but less than 50° C., at a pH of from 7.0 to 7.9 and at an ionic strength of from 0.027 to 0.20 for a time sufficient to allow 100% lysis of said bacteria in a mixture containing 12% of a normal human serum standard under the same conditions of temperature, ionic strength, and pH at which said mixture is incubated; and
    (b) detecting said assayable component released into solution during said incubating.

2. A method of determining the activity of complement in a sample, which comprises:
    (a) incubating a mixture comprising (1) an aqueous suspension of *E. coli* ATCC 39056 bacteria at a concentration of from $10^5$ to $10^9$ cells/ml, said cells containing an assayable intracellular component, and (2) said sample, wherein said mixture contains from 0.2 to 50% by volume of said sample and said incubating is conducted at a temperature of at least 4° C. but less than 50° C., at a pH of from 7.0 to 7.9 and at an ionic strength of from 0.027 to 0.20 for a time sufficient to allow 100% lysis of said bacteria in a mixture containing 12% of a normal human serum standard under the same conditions of temperature, ionic strength, and pH at which said mixture is incubated; and
    (b) detecting said assayable component released into solution during said incubating.

3. The method of claim 2, which, prior to said step (a), further comprises incubating said sample with a predetermined amount of complement under conditions effective to complex any antibody/antigen complexes present in said sample, and after said step (b) further comprises determining the amount of antigen or antibody originally present in said sample from the extent of lysis of said bacteria.

4. The method of claims 2, 3 or 1 wherein said sample is animal serum.

5. The method of claim 4 wherein said animal is a human.

6. The method of claim 2, 3 or 1 wherein said component is an enzyme.

7. The method of claim 2, 3 or 1 wherein the concentration of intracellular component in said bacteria is substantially higher than normal concentrations thereof in said bacteria.

8. The method of claim 7, wherein said concentration has increased by induction.

9. The method of claim 2, 3 or 1 wherein said detection is an enzyme assay.

10. The method of claim 2, 3 or 1 wherein said sample is human serum, said bacteria is induced to produce higher than normal concentrations of $\beta$-galactosidase, and wherein said detection is carried out by assaying said $\beta$-galactosidase with O-nitrophenylgalactoside.

11. A kit which comprises a carrier means being compartmentalized to receive in close confinement one or more container means, wherein one container means contains *E. coli* ATCC 39056 bacteria containing $\beta$-galactosidase as an intracellular enzyme and said kit also comprises either in said container means or in a second container means a substrate for $\beta$-galactosidase and wherein the amount of said bacteria and said substrate are sufficient to determine the bacteriolytic capacity of a sample containing sufficient antibody to said bacteria and sufficient complement to lyse said bacteria and release said intracellular enzyme.

12. The kit of claim 11, wherein the concentration of $\beta$-galactosidase in said bacteria is substantially higher than normal concentrations thereof in said bacteria.

13. The kit of claim 12, wherein said concentration has been increased by induction.

14. The kit of claim 11 which further comprises a container means containing antibody.

15. The kit of claim 11 wherein said first container means contains said bacteria in freeze-dried form.

16. The kit of claim 11, which further comprises a container means containing complement.

* * * * *